(12) United States Patent
Mozeleski et al.

(10) Patent No.: US 6,881,859 B2
(45) Date of Patent: Apr. 19, 2005

(54) TRIALKYL ACETIC ACID (NEO ACID) ESTERS AND ESTERIFICATION PROCESS

(75) Inventors: Edmund John Mozeleski, Califon, NJ (US); Richard Henry Schlosberg, Bridgewater, NJ (US); George A. Knudsen, Scotch Plains, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/215,104

(22) Filed: Aug. 8, 2002

(65) Prior Publication Data

US 2004/0030168 A1 Feb. 12, 2004

(51) Int. Cl.[7] .......................... C07C 67/02; C07C 67/00
(52) U.S. Cl. ....................................... 560/265; 554/124
(58) Field of Search ........................... 560/265; 554/124

(56) References Cited

U.S. PATENT DOCUMENTS

| | | | |
|---|---|---|---|
| 3,037,052 A | 5/1962 | Bortnick | 260/785 |
| 3,349,107 A | 10/1967 | Pawlenko | 260/410.9 |
| 4,332,738 A | 6/1982 | Benitez et al. | 260/410.6 |

FOREIGN PATENT DOCUMENTS

| | | |
|---|---|---|
| GB | 960001 | 6/1964 |
| GB | 998974 | 7/1965 |

OTHER PUBLICATIONS

Coopersmith, et al. *Preparation and Hydrolytic Stability of Trialkylacetic Acid Esters*, I&EC Product Research and Development, vol. 5, No. 1 (1966).
*The Journal of the American Oil Chemists Society*, 45, No. 1, Jan. 1968, pp. 5–10.
H. Koch, *Brennstoff Chem.* 36, 321 (1955).

*Primary Examiner*—Paul A. Zucker
(74) *Attorney, Agent, or Firm*—Lucinda Lomas

(57) ABSTRACT

Disclosed is a method of making trialkyl acetic acid ("neo acid") esters and a neo acid ester composition. Neo acid esters are made by contacting a neo acid stream, comprising a mixture of neo acids, with alcohol in the presence of a catalyst. The invention has the benefit of providing a desired neo acid ester composition, while eliminating, or at least limiting, the need for separation and/or purification of the reactants prior to the synthesis of the desired neo acid esters.

32 Claims, No Drawings

TRIALKYL ACETIC ACID (NEO ACID) ESTERS AND ESTERIFICATION PROCESS

FIELD OF THE INVENTION

This invention is to trialkyl acetic acid ("neo acid") esters and methods of esterifying neo acids. More specifically, this invention is to selective esterification of neo acids.

BACKGROUND OF THE INVENTION

Neo acids are difficult to esterify by common techniques due to the steric effects of the alpha-carbon alkyl groups. Nevertheless, many methods have been disclosed for manufacturing neo acid esters.

Coopersmith, et al., *Preparation and Hydrolytic Stability of Trialkylacetic Acid Esters*, I&EC Product Research and Development, Vol. 5, No. 1 (1966), report that neo acids are esterified using an acid catalyst to increase the rate of the esterification reaction, and an entrainer and molecular sieve to remove water produced during the esterification reaction. The study also reports that the rate of esterification can be adjusted by varying the type and concentration of the catalyst and by selection of the entrainer. This report specifically concentrates on esterification reactions involving neo-pentanoic acid and neo-heptanoic acid.

U.S. Pat. No. 4,332,738 to Benitez et. al. closes a process for direct esterification of a neo acid (having 5 to 28 carbon atoms) with an alcohol in a non-aqueous system in the presence of a macro-reticular structured sulfonic acid cation exchange resin. This process allows esterification under mild conditions (50° C. to 70° C.) by mixing stoichiometric amounts of the desired reactant neo acid with the desired reactant alcohol. The preferred neo acids include neo-pentanoic acid and neo-decanoic acid.

In general, conventional neo acid esterification processes require complex purification procedures, prior to the esterification reactions, to obtain the required neo acid for esterification. Reducing the need for these prior purification procedures would be valuable in saving time and energy and in reducing overall manufacturing complexity and cost. Accordingly, new neo acid esterification processes are desired.

SUMMARY OF THE INVENTION

This invention provides a method of making neo acid esters and provides a neo acid ester composition. A novel aspect of this invention is utilization of a mechanism of "selective esterification." Specifically, this invention eliminates, or at least limits, the need for separation or purification of reactants prior to synthesis of the desired neo acid esters. In addition, separation of the neo acid esters from neo acids remaining in a neo acid mixture is a simpler separation procedure than purification for a single neo acid from the neo acid mixture.

In one embodiment, a method of making neo acid esters is provided. The method comprises providing a neo acid stream and providing at least one alcohol of the formula R'OH, wherein R' is a hydrocarbyl group containing from 1 to 10 carbons. The method further comprises contacting the neo acid stream and the alcohol in a reactor with an acid catalyst to form a product stream, which includes neo acid esters and unreacted neo acids. From 50 wt % to 99 wt % of neo acids in the neo acid stream react with the alcohol to form the neo acid esters.

Desirably, the neo acid stream includes from 50 wt % to 99 wt % $C_5$ neo acid. In another embodiment, the neo acid stream includes not greater than 50 wt % $C_9$ neo acid. In another embodiment, the neo acid stream includes not greater than 20 wt % $C_6$ neo acid. In another embodiment, the neo acid stream includes not greater than 20 wt % $C_7$ neo acid, not greater than about 20 wt % $C_8$ neo acid, and not greater than about 30 wt % $C_{13}$ neo acid.

Desirably, $C_5$ to $C_{11}$ neo acids react with the alcohol to form the neo acid esters. In a more desirable embodiment, $C_5$ to $C_8$ neo acids react with the alcohol to form the neo acid esters. In yet a more desirable embodiment $C_5$ and $C_6$ neo acids react with the alcohol to form the neo acid esters. In an even more desirable embodiment, $C_5$ neo acid reacts with methanol to form methyl pivalate.

The neo acid stream, in a desirable embodiment, includes from 65 wt % to 99 wt % of the neo acids that react with the alcohol. In a more desirable embodiment, the neo acid stream includes from 80 wt % to 99 wt % of the neo acids that react with the alcohol.

It is preferable that the alcohol is an alcohol having from 1 to 5 carbons. Even more preferably, the alcohol is methanol.

In one embodiment, the acid catalyst is a heterogeneous esterification catalyst. In another embodiment, the acid catalyst is a sulfonic acid cation exchange resin having a macro-reticular structure.

In one embodiment the acid catalyst is a homogenous esterification catalyst. In another embodiment, the acid catalyst is 4-toluene sulfonic acid monohydrate.

In an embodiment, the reactor is at a temperature of from ambient temperature to 250° C.

In a preferable embodiment, the method of making the neo acid esters further comprises separating the product stream into a first fraction, which includes at least 50 wt % of the neo acid esters of the product stream, and a second fraction, which includes at least 50 wt % of the unreacted neo acids of the product stream. In another embodiment, the method of making the neo acid esters further comprises separating the second fraction by distillation to produce a recycle stream which includes at least 50 wt % of the unreacted neo acids that are able to react with the alcohol to form neo acid esters. In another embodiment, the method of making the neo acid esters further comprises recycling the recycle stream to the reactor.

In one embodiment the product stream further includes water and unreacted alcohol, and the first fraction includes at least 50 wt % of the neo acid esters, at least 50 wt % of the water, and at least 50 wt % of the unreacted alcohol. The method of making the neo acid ester further comprises distilling at least 50 wt % of the unreacted alcohol from the first fraction and separating at least 50 wt % of the water from the first fraction. Preferably, separating the water is by phase separation. Optionally, separating the water includes using a water-insoluble azeotroping solvent to remove the water.

In another embodiment, a method of making neo acid esters is provided. The method comprises providing a neo acid stream, including unhindered neo acids and sterically hindered neo acids, and providing at least one alcohol. The method further comprises esterifying the unhindered neo acids in the neo acid stream. In a preferred embodiment the neo acid stream includes not greater than 50 wt % of the sterically hindered neo acids. In another preferred embodiment, the unhindered neo acid is pivalic acid. In still another preferred embodiment, the alcohol is methanol.

In yet another embodiment, a neo acid ester composition is provided, comprising 60 to 99 wt % methyl pivalate; 0.25 to 10 wt % $C_6$ to $C_8$ neo acid esters; 0.25 to 20 wt % $C_9$ to $C_{13}$ neo acid esters; 0.25 to 4 wt % $C_6$ to $C_8$ neo acids; and 0.25 to 6 wt % $C_9$ to $C_{13}$ neo acids. In one preferred embodiment, the neo acid ester composition further comprises 1 to 39 wt % water. In anther preferred embodiment, the neo acid ester composition further comprises 1 to 10 wt % alcohol.

DETAILED DESCRIPTION OF THE INVENTION

This invention provides a method of making neo acid esters. The esters are made by contacting a neo acid stream, comprising a mixture of neo acids, with at least one alcohol in the presence of a catalyst.

Neo acids are trialkyl acetic acids, which include a tetra substituted alpha-carbon. Alkyl groups on the substituted alpha-carbon create a steric effect, i.e. hinder the ability of the neo acid to react. Methyl substituted alpha-carbon neo acids are the least hindered of the neo-acids. The reactivity of the neo acid primarily depends on the molecular weight and structure of the neo acid, but may also depend on the molecular weight and structure of a provided reagent. In general, the greater the molecular weight of the alkyl groups on the alpha-carbon, the greater the steric effect and the less reactive the neo acid. Conversely, in general, the fewer carbons comprising the neo acid and the simpler the alcohol provided for esterification, the less hindered the reaction.

For the purposes of this invention, the neo acids in a neo acid stream that do not substantially react with the alcohol provided are referred to as hindered or sterically hindered neo acids; the neo acids in the neo acid stream that do substantially react in the presence of the alcohol provided are referred to as unhindered neo acids.

This invention is particularly desirable because of the difficulties associated with separating neo acids in a neo acid mixture. Selective esterification provides for more efficient separations between the neo acid esters and the unreacted neo acids, as compared to the neo acid separations in the prior art that were necessary prior to the esterification step.

The reaction of a neo acid and an alcohol yields a neo acid ester product composition, comprising neo acid esters. A novel aspect of this invention is the ability to utilize the steric effects of the neo acids to esterify only those neo acids in the neo acid stream that are unhindered. This mechanism is referred to as "selective esterification" in explaining the details of this invention. Selective esterification is defined as esterification of the unhindered neo acids in a neo acid stream containing unhindered neo acids and hindered neo acids. In effect, the neo acids in the neo acid stream that are of the lowest molecular weight are typically the least hindered, and, therefore, esterified most readily. Preferably, $C_5$ to $C_{11}$ neo acids are selectively esterified by the alcohol present. More preferably, $C_5$ to $C_8$ neo acids are selectively esterified. Even more preferably, $C_5$ to $C_6$ neo acids are selectively esterified. Most preferably, $C_5$ neo acid, also known as pivalic acid and defined as 2,2,2-trimethyl acetic acid, is selectively esterified.

Under favorable esterification conditions, preferably, not greater than about 50 wt % of the neo acids in the neo acid stream are unreactive with the alcohol provided. More preferably, not greater than about 35 wt % of the neo acids in the neo acid stream are unreactive with the alcohol provided. Most preferably, not greater than about 20 wt % of the neo acids in the neo acid stream are unreactive with the alcohol provided.

The neo acid stream, comprising a mixture of neo acids, may be obtained from any conventional source. The preferred neo acid stream includes from about 50 wt % to about 99 wt % of unhindered neo acids that react with the alcohol provided. More preferably, the neo acid stream includes from about 65 wt % to about 99 wt % of unhindered neo acids. Most preferably, the neo acid stream includes from about 80 wt % to about 99 wt % of unhindered neo acids.

In one embodiment the neo acid stream includes from about 50 wt % to about 99 wt % of $C_5$ neo acid. More preferably, the neo acid stream includes from about 65 wt % to about 99 wt % of $C_5$ neo acid. Most preferably, the neo acid stream includes from about 80 wt % to about 99 wt % of $C_5$ neo acid.

In one embodiment the neo acid stream includes not greater than about 20 wt % of $C_6$ neo acid. More preferably, the neo acid stream includes not greater than about 10 wt % of $C_6$ neo acid. Most preferably, the neo acid stream includes not greater than about 5 wt % of $C_6$ neo acid.

In another embodiment the neo acid stream includes not greater than about 20 wt % of $C_7$ neo acid. More preferably, the neo acid stream includes not greater than about 10 wt % of $C_7$ neo acid. Most preferably, the neo acid stream includes not greater than about 5 wt % of $C_7$ neo acid.

In yet another embodiment the neo acid stream includes not greater than about 20 wt % of $C_8$ neo acid. More preferably, the neo acid stream includes not greater than about 10 wt % of $C_8$ neo acid. Most preferably, the neo acid stream includes not greater than about 5 wt % of $C_8$ neo acid.

In still another embodiment the neo acid stream includes not greater than about 50 wt % of $C_9$ neo acid. More preferably, the neo acid stream includes from about 5 wt % to about 40 wt % of $C_9$ neo acid. Most preferably, the neo acid stream includes from about 10 wt % to about 30 wt % of $C_9$ neo acid.

In yet still another embodiment the neo acid stream includes not greater than about 30 wt % of $C_{13}$ neo acid. More preferably, the neo acid stream includes not greater than about 15 wt % of $C_{13}$ neo acid. Most preferably, the neo acid stream includes not greater than about 10 wt % of $C_{13}$ neo acid.

In a preferred embodiment, $C_{13}+$ neo acids present in the neo acid stream are hindered neo acids that do not substantially react in the presence of the alcohol provided. Preferably, less than about 40 wt % of the $C_{13}+$ neo acids present in the neo acid stream react with the alcohol provided. More preferably, less than about 30 wt % of the $C_{13}+$ neo acids react with the alcohol provided. Most preferably, less than about 15 wt % of the $C_{13}+$ neo acids react with the alcohol provided.

In a preferred embodiment, $C_9$ neo acid present in the neo acid stream is a hindered neo acid that does not substantially react in the presence of the alcohol provided. Preferably, less than about 25 wt % of the $C_9$ neo acid present in the neo acid stream reacts with the alcohol provided. More preferably, less than about 20 wt % of the $C_9$ neo acid reacts with the alcohol provided. Most preferably, less than about 15 wt % of the $C_9$ neo acid reacts with the alcohol provided.

In a preferred embodiment, $C_8$ neo acid present in the neo acid stream is a hindered neo acid that does not substantially react in the presence of the alcohol provided. Preferably, less than about 25 wt % of the $C_8$ neo acid present in the neo acid stream reacts with the alcohol provided. More preferably, less than about 20 wt % of the $C_8$ neo acid reacts with the alcohol provided. Most preferably, less than about 15 wt % of the $C_8$ neo acid reacts with the alcohol provided.

In another embodiment, $C_7$ neo acid present in the neo acid stream is a hindered neo acid that does not substantially react in the presence of the alcohol provided. Preferably, less than about 30 wt % of the $C_7$ neo acid present in the neo acid stream reacts with the alcohol provided. More preferably, less than about 25 wt % of the $C_7$ neo acid reacts with the alcohol provided. Most preferably, less than about 20 wt % of the $C_7$ neo acid reacts with the alcohol provided.

In yet another embodiment, $C_6$ neo acid present in the neo acid stream is a hindered neo acid that does not substantially react in the presence of the alcohol provided. Preferably, less than about 70 wt % of the $C_6$ neo acid present in the neo acid stream reacts with the alcohol provided. More preferably, less than about 40 wt % of the $C_6$ neo acid reacts with the alcohol provided. Most preferably, less than about 25 wt % of the $C_6$ neo acid reacts with the alcohol provided.

In one embodiment, $C_5$ to $C_{11}$ neo acids are unhindered neo acids that substantially react in the presence of the alcohol provided. Preferably, about 50 wt % to about 99 wt % of the $C_5$ to $C_{11}$ neo acids react with the alcohol provided. More preferably, about 65 wt % to about 99 wt % of the $C_5$ to $C_{11}$ neo acids react with the alcohol provided. Most preferably, about 80 wt % to about 99 wt % of the $C_5$ to $C_{11}$ neo acids react with the alcohol provided.

In another embodiment, $C_5$ to $C_8$ neo acids are unhindered neo acids that substantially react in the presence of the alcohol provided. Preferably, about 65 wt % to about 99 wt % of the $C_5$ to $C_8$ neo acids react with the alcohol provided. More preferably, about 80 wt % to about 99 wt % of the $C_5$ to C8 neo acids react with the alcohol provided. Most preferably, about 90 wt % to about 99 wt % of the $C_5$ to $C_8$ neo acids react with the alcohol provided.

In another embodiment, $C_5$ and $C_6$ neo acids are unhindered neo acids that substantially react in the presence of the alcohol provided. Preferably, about 70 wt % to about 99 wt % of the $C_5$ and $C_6$ neo acids react with the alcohol provided. More preferably, about 85 wt % to about 99 wt % of the $C_5$ and $C_6$ neo acids react with the alcohol provided. Most preferably, about 95 wt % to about 99 wt % of the $C_5$ and $C_6$ neo acids react with the alcohol provided.

In yet another embodiment, $C_5$ neo acid is an unhindered neo acid that substantially reacts in the presence of the alcohol provided. Preferably, about 80 wt % to about 99 wt % of the $C_5$ neo acid reacts with the alcohol provided. More preferably, about 90 wt % to about 99 wt % of the $C_5$ neo acid reacts with the alcohol provided. Most preferably, about 95 wt % to about 99 wt % of the $C_5$ neo acid reacts with the alcohol provided.

In one embodiment monohydric alcohols having from 1 to 10 carbons are reactive with the unhindered neo acids. Preferably, at least about 80 wt % of the alcohols are reactive. More preferably, at least about 90 wt % of the alcohols are reactive. Most preferably, at least about 99 wt % of the alcohols are reactive.

In another embodiment monohydric alcohols having from 1 to 5 carbons are reactive with the unhindered neo acids. Preferably, at least about 80 wt % of the alcohols are reactive. More preferably, at least about 90 wt % of the alcohols are reactive. Most preferably, at least about 99 wt % of the alcohols are reactive.

In another embodiment methanol is reactive with the unhindered neo acids. Preferably, at least about 80 wt % of the methanol is reactive. More preferably, at least about 90 wt % of the methanol is reactive. Most preferably, at least about 99 wt % of the methanol is reactive.

The neo acids included in the mixture may be expressed according to Formula I:

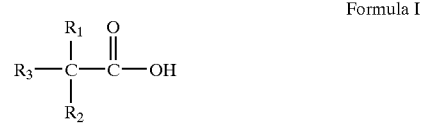

Formula I where, preferably, each of $R_1$, $R_2$, and $R_3$ is an alkyl group having from 1 to 10 carbons, and the total carbons in $R_1+R_2+R_3$ is from 3 to 30. More preferably, each of $R_1$, $R_2$, and $R_3$ is an alkyl group having from 1 to 7 carbons, and the total carbons in $R_1+R_2+R_3$ is from 3 to 21. Even more preferably, each of $R_1$, $R_2$, and $R_3$ is an alkyl group having from 1 to 3 carbons, and the total carbons in $R_1+R_2+R_3$ is from 3 to 9. Most preferably, each of $R_1$, $R_2$, and $R_3$ is a methyl group.

The neo acids of Formula I are commercially available and are commonly referred to as alpha-branched carboxylic acids, synthetic trialkyl acetic acids, or tertiary carboxylic acids (see *The Journal of the American Oil Chemists Society*, 45, No. 1, January 1968, pages 5–10). The neo acids can be prepared by the well known Koch process from olefins, carbon monoxide and water as described by H. Koch in *Brennstoff Chem*. 36, 321 (1955). Further details on methods for making neo acids useful herein as Formula I compounds are found in British Patent Nos. 960,001 and 998,974, and U.S. Pat. No. 3,349,107, each incorporated fully herein by reference.

Neo acids used in this invention can be made from an olefin feedstock, which for $C_5$ and higher olefins can be random isomeric mixtures in regard to the position of the olefinic bond. Thus, the neo acids produced from the olefin feedstock may be random isomeric mixtures of neo acids. A benefit of selective esterification is that minimal separations are needed prior to esterification. At a minimum, contaminants that may affect the reaction or be difficult to remove after esterification should be removed.

In this invention, the neo acids react with alcohol to make the neo acid esters. Preferably, the alcohol esterifies $C_5$ to $C_1$, neo acids. More preferably, the alcohol esterifies $C_5$ to $C_8$ neo acids. Even more preferably, the alcohol esterifies $C_5$ to $C_6$ neo acids. Most preferably, the alcohol esterifies $C_5$ neo acids.

Useful monohydric alcohols which can be used in the reaction of this invention can be characterized by the formula R'OH where R' is a hydrocarbyl group containing from 1 to 10 carbons. Such hydrocarbyl groups may include methyl, ethyl, n-propyl, isopropyl, n-butyl, sec-butyl, isobutyl, tert-butyl, n-pentyl, sec-pentyl, iso-pentyl, tert-pentyl, other univalent isomers, and mixtures thereof. More preferably, the hydrocarbyl group contains 1 to 5 carbons. Most preferably, the hydrocarbyl group contains 1 carbon.

In one embodiment the alcohol includes at least 60 wt % methanol. More preferably, the alcohol includes at least about 70 wt % methanol. Most preferably, the alcohol includes at least about 80 wt % methanol.

In another embodiment the alcohol includes not more than about 30 wt % ethanol. More preferably, the alcohol includes not more than about 20 wt % ethanol. Most preferably, the alcohol includes not more than about 10 wt % ethanol.

In still another embodiment the alcohol includes not more than about 20 wt % propanol. More preferably, the alcohol includes not more than about 15 wt % propanol. Most preferably, the alcohol includes not more than about 10 wt % propanol.

The reactants may be contacted in the presence of a heterogeneous or a homogenous acid catalyst. The acid catalyst is used to increase the rate of reaction. The amount of catalyst is not critical, but at least enough catalyst must be used to provide a reasonable rate of esterification.

A conventional heterogeneous esterification catalyst may be used. One preferred heterogeneous catalyst that may be used is a sulfonic acid cation exchange resin having a macro-reticular structure. These catalysts, their properties, and method of preparation are shown in U.S. Pat. No. 3,037,052. Such catalysts are available commercially and are sold under the trade name Amberlyst by Rohm & Haas of Philadelphia, Pa. Acidic zeolite catalysts may also be used.

Alternatively, a conventional homogenous esterification acid catalyst may be utilized in the reaction. Useful catalysts include sulfuric acid, phosphoric acid, p-toluene sulfonic acid, sodium bisulfate, potassium bisulfate, related catalysts, and the like. Other catalysts that may be used include esters of titanium or zirconium, such as tetraalkyl titanates or zirconates (e.g. tetraethyl titanate, tetraisopropyl titanate, tetrabutyl titanate, tetra-n-propyl zirconate, etc). Also metal oxides such as zinc oxide, alumina, and the like can be used. A preferred homogenous catalyst is 4-toluene sulfonic acid monohydrate.

Preferably, the reaction is carried out in a non-aqueous system with less than or equal to about 5 wt % water. More preferably, the reaction is carried out in a non-aqueous system with less than or equal to about 2 wt % water. Most preferably, the reaction is carried out in a non-aqueous system with less than or equal to about 0.5 wt % water.

The reaction can be carried out in either a batch or continuous manner, such as in a continuously stirred tank reactor or tubular reactor, which may be temperature controlled. In the batch process, the reactants, products, and catalyst are separated by conventional methods. If a resin catalyst is used, it can be reused for subsequent esterification reactions.

Preferably, reaction conditions are provided to drive the esterification of the neo acids to completion. For example, an excess of a reactants may be provided, and/or the reaction products may be removed as they are produced. Reaction conditions and reactants are provided so as to minimize the amount of excess alcohol. Preferably, at least about 80% of the alcohol is reacted. More preferably, at least about 90% of the alcohol is reacted. Most preferably, at least about 99% of the alcohol is reacted.

Conventional esterification reaction conditions can be used. Preferably, reactor temperature may range from about ambient temperature to about 250° C., more preferably from about 50° to about 220° C., most preferably from about 100° to about 220° C., until the reaction is substantially complete. Temperatures above about 250° C. are only necessary when esterification of sterically hindered reagents is desired. In general, temperatures above about 250° C. should be avoided to avoid catalyst degradation. Completion of reaction may be determined by gas chromatography analysis of the product composition.

In one embodiment, the neo acid ester product composition includes at least one neo acid ester selectively esterified from the neo acid mixture. Preferably, the composition includes at least one $C_5$ to $C_{11}$ neo acid ester. More preferably, the composition includes at least one $C_5$ to $C_8$ neo acid ester. Even more preferably, the composition includes at least one $C_5$ to $C_6$ neo acid ester. Most preferably, the composition includes methyl pivalate, defined as 2,2,2-trimethyl acetic acid methyl ester.

In another embodiment, the neo acid ester product composition includes at least about 10 wt % of at least one neo acid ester selectively esterified from the neo acid mixture. More preferably, the neo acid ester product composition includes at least about 50 wt % of at least one neo acid ester selectively esterified from the neo acid mixture. Most preferably, the neo acid ester composition includes at least about 90 wt % of at least one neo acid ester selectively esterified from the neo acid mixture.

In a preferred embodiment, the neo acid ester product composition is separated into at least two fractions after reaction. Preferably, the first fraction includes at least about 50 wt % of the neo acid esters in the neo acid ester product composition. More preferably, the first fraction includes at least about 75 wt % of the neo acid esters. Most preferably, the first fraction includes at least about 95 wt % of the neo acid esters.

Preferably, the second fraction includes at least about 50 wt % of the unreacted, hindered neo acids and unreacted, unhindered neo acids in the neo acid ester product composition. More preferably, the second fraction includes at least about 75 wt % of the unreacted, hindered neo acids and unreacted, unhindered neo acids. Most preferably, the second fraction includes at least about 95 wt % of the unreacted, hindered neo acids and unreacted, unhindered neo acids.

The second fraction may be further distilled to produce a recycle stream of the unreacted, unhindered neo acids. Preferably, the recycle stream includes at least about 50 wt % of the unreacted, unhindered neo acids. More preferably, the recycle stream includes at least about 75 wt % of the unreacted, unhindered neo acids. Most preferably, the recycle stream includes at least about 90 wt % of the unreacted, unhindered neo acids. The recycle stream may be recycled to the reactor.

Preferably, the reactants are combined and reacted such that, upon separation of the neo acid esters from the by-products and reactants, little additional processing is needed. However, additional separations may be required to obtain desirable characteristics. Separation may be by distillation, solvent extraction by absorption of undesirable by-products using molecular sieves, or by any other equivalent processing method. Removal of undesired quantities of acid and moisture can be accomplished by further treatment, such as filtering the product with a filter aid or contacting the product with a molecular sieve. Optionally, a water-insoluble, azeotroping solvent may be used to remove water formed during the reaction. Such solvents may include aliphatic or aromatic hydrocarbons, or other water-insoluble, azeotroping solvents. Should it be necessary, dilution or other components can be added to the neo acid esters to adjust the fluid composition characteristics.

In one embodiment, neo acid ester product composition includes neo acid esters, water, unreacted alcohol, unreacted, hindered neo acids, and unreacted, unhindered neo acids. The neo acid product composition is separated into two fractions. The first fraction includes the neo acid esters and the second fraction includes the unreacted, hindered neo acids and unreacted, unhindered neo acids.

In addition, the first fraction includes at least about 50 wt % of the water in the neo acid ester product composition. More preferably, the first fraction includes at least about 75 wt % of the water. Most preferably, the first fraction includes at least about 95 wt % of the water.

The first fraction may also include unreacted alcohol in the neo acid ester product composition. Preferably, the first fraction includes at least about 50 wt % of the unreacted alcohol in the neo acid ester product composition. More preferably, the first fraction includes at least about 75 wt % of the unreacted alcohol. Most preferably, the first fraction includes at least about 95 wt % of the unreacted alcohol.

The first fraction may be further separated by distilling the unreacted alcohol from the first fraction. In addition, the water in the first fraction may be separated from the first fraction. Preferably, at least about 50 wt % of the water is separated. More preferably, at least about 75 wt % of the water is separated. Most preferably, at least about 95 wt % of the water is separated. The water may be separated from the neo acid esters by phase separation.

In yet another embodiment, a neo acid ester composition is provided. Preferably, the neo acid ester composition includes about 60 wt % to about 99 wt % methyl pivalate; more preferably, the neo acid ester composition includes about 80 wt % to about 99 wt % methyl pivalate; and, most preferably, the neo acid ester composition includes about 95 wt % to about 99 wt % methyl pivalate.

In one preferred embodiment, the neo acid ester composition includes about 0.25 wt % to about 10 wt % $C_6$ to $C_9$ neo acid esters; more preferably, about 0.25 wt % to about 5 wt % $C_6$ to $C_8$ neo acid esters; and, most preferably, about 0.25 wt % to about 1 wt % $C_6$ to $C_8$ neo acid esters.

In another preferred embodiment, the neo acid ester composition includes about 0.25 wt % to about 20 wt % $C_9$ to $C_{13}$ neo acid esters; more preferably, about 0.25 wt % to about 10 wt % $C_9$ to $C_{13}$ neo acid esters; and, most preferably, about 0.25 wt % to about 1 wt % $C_9$ to $C_{13}$ neo acid esters.

The neo acid ester may also include unreacted reagents. Preferably, the neo acid ester composition includes about 0.25 wt % to about 4 wt % $C_6$ to $C_8$ neo acids; more preferably, about 0.25 wt % to about 1 wt % $C_6$ to $C_8$ neo acids; and, most preferably, about 0.25 wt % to about 0.5 wt % $C_6$ to C8 neo acids.

In another embodiment, the neo acid ester composition includes $C_9$ to $C_{13}$ neo acids. Preferably, the neo acid ester composition includes about 0.25 wt % to about 6 wt % $C_9$ to $C_{13}$ neo acids; more preferably, the neo acid ester composition includes about 0.25 wt % to about 2 wt % $C_9$ to $C_{13}$ neo acids; and, most preferably, the neo acid ester composition includes about 0.25 wt % to about 0.5 wt % $C_9$ to $C_{13}$ neo acids.

In yet another embodiment, the neo acid ester composition includes unreacted alcohol. Preferably, the neo acid ester composition includes about 1 wt % to about 10 wt % alcohol; more preferably, the neo acid ester composition includes about 1 wt % to about 4 wt % alcohol; most preferably, the neo acid ester composition includes about 1 wt % to about 2 wt % alcohol.

Water is a product of the reaction and may also be present in the neo acid ester composition. Preferably, the neo acid ester composition includes about 1 wt % to about 39 wt % water; more preferably, the neo acid ester composition includes about 1 wt % to about 20 wt % water; and most preferably, the neo acid ester composition includes about 1 wt % to about 5 wt % water.

Replacement of certain solvents with neo acid esters and/or neo acid ester compositions may be environmentally beneficial. The neo acid ester composition according to the invention may be used in any process using a fluid and particularly those processes wherein at least a portion of the fluid evaporates and even more particularly wherein at least a portion evaporates into the atmosphere. Preferred processes are those utilizing the fluid as one or more of a carrier, diluent, dispersant, solvent, and the like, including processes wherein the fluid functions as an inert reaction medium in which other compounds react; as a heat-transfer fluid removing heat of reaction; to improve workability of a manufacturing process; as a viscosity reducer to thin coatings; as an extraction fluid to separate one material from another; as a tackifier or to improve adhesion to a substrate for better bonding; as a dissolving medium to prepare solutions of polymers, resins, and other substances; to suspend or disperse pigments and other particulates; and the like.

It is preferred that the process be a stationary process and also preferred that the process be a non-combustion process. It is particularly beneficial if neo acid ester compositions be used to replace at least a portion of a traditional industrial solvent in a process using a large amount of fluid, e.g., a process using about 1000 lb./year (500 kg/year), even more preferably about 5 tons/year (5000 kg/yr.), still more preferably about 50 tons/year (50,000 kg/yr.), and most preferably about one million lbs./year (500,000 kg/yr.).

It is also preferred that the process in which a neo acid ester composition is used be a process in which the fluid is intended to evaporate, such as in a coating process. In such a process where the fluid is intended to evaporate, it is preferred that at least about 10% of the fluid or fluids evaporate, more preferably about 20% of the fluids, and so on, so that it is most preferable if greater than about 99% of the fluid or fluids present in the coating evaporate.

The environmental benefits of replacing a currently-used industrial solvent with the neo acid ester composition according to this invention will be realized if performed in a geographic area where monitoring for ozone and particulate matter formation occurs, and more particularly, in geographic areas defined by a city and its contiguous area by at least about 500,000 persons, and wherein the replacement of at least a portion of the currently-used industrial solvent with a neo acid ester composition according to the invention causes a reduction in the ozone formation.

The invention can be used in fluid compositions in a variety of industrial applications such as paints and other coatings, adhesives, sealants, agricultural chemicals, cleaning solution, consumer products such as cosmetics, pharmaceuticals, drilling muds, extraction, reaction diluents, inks, metalworking fluids, photoresists, etc.

A preferred use of the neo acid ester composition according to the invention is with any process wherein the reduction of ozone formation is desired, and more particularly in consumer products, and coatings such as auto refinishing, architectural and industrial coatings and paints.

The reactivity of a volatile organic compound ("VOC") is expressed as a Maximum Incremental Reactivity (MIR) value. The MIR value for a compound is the measure of the increase in ozone formation per unit weight of a hydrocarbon when added to the atmosphere. In summary, MIR data quantifies ozone impacts of emissions of VOCs. The MIR value for methyl pivalate has a value of 0.49, substantially less than the value of most common VOCs. One skilled in the art would know to find MIR values for common solvents in the public domain. Information, data reports, and related links regarding MIR values can be found at http://pah.cert.ucr.edu/~carter/reactdat.htm#data.

Paints and coatings comprise the largest single category of traditional solvent consumption, accounting for nearly half the solvents used. Fluids serve multiple functions in paints and coatings, including solubility, wetting, viscosity reduction, adhesion promotion, and gloss enhancement. Fluids dissolve the resins, dyes and pigments used in the coating formulations. Also, prior to application, it is common practice to add a solvent thinner to attain the desired viscosity for the particular application. Solvents begin to evaporate as soon as the coating materials are applied. As the solvent evaporates, film formation occurs and a continuous, compact film develops. Single solvents are sometimes used in coatings formulations, but most formulations are blends of several solvents. In many coatings applications, the solvent system includes a slow-evaporating active solvent that remains in the film for an extended period to enhance the film's gloss and smoothness. Because of evaporation and the large amounts of solvents used in coatings, there is a significant amount of VOC emissions into the atmosphere. Complete or partial replacement of solvents with the neo acid ester composition of this invention may by environmentally beneficial.

One cleaning application is cold solvent cleaning which is used to degrease metal parts and other objects in many operations. Mineral spirits have been popular in cold cleaning, but are being supplanted by higher flash point hydrocarbon solvents due to emissions and flammability concerns. Efforts to eliminate organic solvents entirely from cleaning compositions have not been successful because aqueous cleaners do not have the performance properties that make organic solvent based cleaners so desirable. Neo acid ester compositions allow formulators the option to seek the use of solvents with very low reactivity as environmentally preferred products meeting environmental concerns and customer performance concerns.

A cleaning solution application that uses evaporation to clean is called vapor degreasing. In vapor degreasing, the solvents vaporize and the cold part is suspended in the vapor stream. The solvent condenses on the part, and the liquid dissolves and flushes dirt, grease, and other contaminants off the surface. The part remains in the vapor until it is heated to the vapor temperature. Drying is almost immediate when the part is removed and solvent residues are not a problem. The most common solvent used in vapor degreasing operations has been 1,1,1-trichloroethane. However, since 1,1,1-trichloroethane is being phased out due to ozone depletion in the stratosphere, alternatives are needed. Moreover, chlorine-based solvents have toxicity concerns. Thus, neo acid ester compositions can be used in place of 1,1,1-trichloroethane and other halogenated solvents.

An application that is similar to coatings is printing inks. In printing inks, a resin is dissolved in the solvent to produce the ink. Most printing operations use fast evaporating solvents for best production speeds, but the currently used solvents are highly reactive. Neo acid ester compositions may be suitable for printing inks because of its characteristics.

An application that is suitable to neo acid ester compositions, due to its low toxicity, high flash point and low reactivity in ozone formation, is agricultural products. Pesticides are frequently applied as emulsifiable concentrates. The active insecticide or herbicide is dissolved in a solvent, which also contains an emulsifier. Solvent selection is critical for this application. It can seriously impact the efficiency of the formulation. The solvent should have adequate solvency for the pesticide, promote good dispersion when diluted with water, have low toxicity and a flash point high enough to minimize flammability hazards.

Extraction processes, used for separating one substance from another, are commonly employed in the pharmaceutical and food processing industries. Oilseed extraction is a widely used extraction process. Extraction-grade hexane is a common solvent used to extract oil from soybeans, cottonseed, corn, peanuts, and other oil seeds to produce edible oils and meal used for animal feed supplements. Neo acid ester compositions may be useful in such industries.

The neo acid ester compositions of this invention can be used as a solvent for various positive or negative type photoresists. Such compositions comprise an alkali-soluble resin, a radiation sensitive resin, and the neo acid ester compositions of this invention. In this use, the neo acid ester composition is a solvent for the combination of the alkali-soluble resin and the radiation sensitive resin. Typical alkali-soluble resins include alkali-soluble novolaks, polyhydroxystyrenes and their derivatives, styrene-maleic anhydride copolymers, polyvinyl hydroxybenzoates, carboxyl group-containing methacrylate resins, and combinations thereof. Typical radiation sensitive resins include 1,2-quinonediazide compounds and azide compounds. Preferred are 1,2-quinonediazide acid esters of polyhydroxy compounds having at least 3 hydroxyl groups, preferably 4 hydroxyl groups.

In addition to the above-mentioned applications, other applications that can use high flash point, low toxicity, low reactivity in ozone formation neo acid ester compositions are adhesives, sealants, cosmetics, drilling muds, reaction diluents, metal working fluids, and consumer products, such as pharmaceuticals or cosmetics.

This invention will be better understood with reference to the following examples, which are intended to illustrate specific embodiments within the overall scope of the invention as claimed:

EXAMPLE 1

A neo acid mixture (1.5 ml) containing pivalic acid was added to a 3 dram vial and contacted with methanol (1.5 ml) in the presence of 4-toluene sulfonic acid monohydrate (0.2 g). The liquid solution was sampled and analyzed by gas chromatography before and after esterification. Table 1 is a comparison of the gas chromatography results. (The results are area percentages and no response factors were used.):

TABLE 1

Comparison of Reactant and Product Compositions

| Components | Reactant Composition wt % | Product Composition wt % | Conversion of Acid to Ester % |
|---|---|---|---|
| Methyl pivalate | — | 69.80 | 96.5 |
| $C_6$ neo acid ester | — | 0.98 | 64.4 |
| $C_7$ neo acid ester | — | 0.20 | 26.7 |
| $C_8$ neo acid ester | — | 0.03 | 20.0 |
| $C_9$ esters | — | 2.50 | 21.3 |
| $C_{13}$ esters | — | 1.10 | 36.7 |
| Pivalic acid | 67.29 | 2.50 | |
| $C_6$ neo acid | 1.52 | 0.54 | |
| $C_7$ neo acid | 0.76 | 0.55 | |
| $C_8$ neo acid | 0.19 | 0.12 | |
| $C_9$ acids | 20.50 | 9.20 | |
| $C_{13}$ acids | 7.43 | 1.90 | |

The results shown in Table 1 demonstrate the selective esterification of pivalic acid to methyl pivalate.

EXAMPLE 2

A column (7 mm×210 mm) was charged with 2.94 g of Amberlyst 35 dry and 8.0 g a neo acid/methanol solution. The solution included 10 wt % of a neo acid mixture. The solution was added to the column at room temperature, and nitrogen was used to pressurize the column. The residence time of the solution was about 2 minutes. The effluent was collected and analyzed by gas chromatography. Such effluent contained 0.564 g methyl pivalate.

The product yield of methyl pivalate corresponded to 73.7 mole % of the theoretical yield of methyl pivalate. As illustrated in this example, esterification of pivalic acid (a $C_5$ neo acid ester) occurred at a significant rate of conversion.

EXAMPLE 3

A neo acid mixture (0.40 g) containing 0.31 g (3.1 mm) pivalic acid was added to a 3 dram vial and treated with methanol (0.61 g, 19 mm) in the presence of 4-toluene sulfonic acid monohydrate (0.10 g, 0.53 mm). The solution was warmed to approximately 50° C. and allowed to stand at room temperature for 24 hours. An internal standard was added, and the mixture was analyzed by gas chromatography.

The solution contained methyl pivalate (0.31 g, 0.0027 m) that corresponded to 86.4 mole % of the theoretical yield of methyl pivalate. As illustrated in this example, esterification of pivalic acid (a $C_5$ neo acid ester) occurred at a significant rate of conversion.

Having now fully described this invention, it will be appreciated by those skilled in the art that the invention can be performed within a wide range of parameters within what is claimed, without departing from the spirit and scope of the invention.

We claim:

1. A method of making neo acid esters, comprising:
   providing a neo acid stream comprising a random isomeric mixture of hindered neo acids and unhindered neo acids, wherein the neo acid stream has not previously been purified to obtain a particular neo acid from the mixture;
   providing at least one alcohol of the formula R'OH, wherein R' is a hydrocarbyl group containing from 1 to 10 carbons; and
   contacting the neo acid stream and the alcohol in a reactor with an acid catalyst to form a product stream which includes at least one unhindered neo acid esters selectively esterified from the neo acid mixture, and unreacted neo acids.

2. The method of claim 1, wherein the neo acid stream includes from 50 wt % to 99 wt % $C_5$ neo acid.

3. The method of claim 2, wherein the neo acid stream includes not greater than 50 wt % $C_9$ neo acid.

4. The method of claim 2, wherein the neo acid stream includes not greater than 20 wt % $C_6$ neo acid.

5. The method of claim 2, wherein the neo acid stream includes not greater than 20 wt % $C_7$ neo acid; not greater than about 20 wt % $C_8$ neo acid; and not greater than 30 wt % $C_{13}$ neo acid.

6. The method of claim 1, wherein $C_5$ to $C_{11}$ neo acids are selectively esterified with the alcohol to form the at least one neo acid esters selectively esterified from the neo acid mixture.

7. The method of claim 6, wherein $C_5$ to $C_8$ neo acids are selectively esterified with the alcohol to form the at least one neo acid esters selectively esterified from the neo acid mixture.

8. The method of claim 7, wherein $C_5$ and $C_6$ neo acids are selectively esterified with the alcohol to form the at least one neo acid esters selectively esterified from the neo acid mixture.

9. The method of claim 8, wherein $C_5$ neo acid is selectively esterified with methanol to form methyl pivalate from the neo acid mixture.

10. The method of claim 1, wherein the neo acid stream includes from 65 wt % to 99 wt % unhindered-neo acids that are selectively esterified with the alcohol to form the at least one neo acid ester selectively esterified from the neo acid mixture.

11. The method of claim 10, wherein the neo acid stream includes from 80 wt % to 99 wt % unhindered-neo acids that are selectively esterified with the alcohol to form the at least one neo acid ester selectively esterified from the neo acid mixture.

12. The method of claim 1, wherein the alcohol is an alcohol having from 1 to 5 carbons.

13. The method of claim 12, wherein the alcohol is methanol.

14. The method of claim 1, wherein the acid catalyst is a heterogeneous esterification catalyst.

15. The method of claim 14, wherein the acid catalyst is a sulfonic acid cation exchange resin having a macroreticular structure.

16. The method of claim 1, wherein the acid catalyst is a homogenous esterification catalyst.

17. The method of claim 16, wherein the acid catalyst is 4-toluene sulfonic acid monohydrate.

18. The method of claim 1, wherein the reactor is at a temperature of from ambient temperature to 250° C.

19. The method of claim 1, further comprising: separating the product stream into a first fraction, which includes at least 50 wt % of the neo acid esters of the product stream, and a second fraction, which includes at least 50 wt % of the unreacted neo acids of the product stream.

20. The method of claim 19, further comprising:
   separating the second fraction by distillation to produce a recycle stream which includes at least 50 wt % of the unreacted unhindered neo acids present in the second fraction.

21. The method of claim 20, further comprising:
   recycling the recycle stream to the reactor.

22. The method of claim 19, wherein the product stream further includes water and unreacted alcohol, and wherein the first fraction includes at least 50 wt % of the water, and at least 50 wt % of the unreacted alcohol present in the product stream.

23. The method of claim 22, further comprising:
   distilling off at least 50 wt % of the unreacted alcohol from the first fraction; and separating at least 50 wt % of the water from the first fraction.

24. The method of claim 23, wherein separating the water is by phase separation.

25. The method of claim 23, wherein separating the water includes using a water-insoluble, azeotroping solvent to remove the water.

26. A method of making neo acid esters, comprising:
   providing a neo acid stream, comprising a random isomeric mixture of sterically hindered neo acids and sterically unhindered neo acids, wherein the neo acid stream has not previously been purified to obtain a particular neo acid from the mixture;
   providing at least one alcohol;
   selectively esterifying at least one of the sterically unhindered neo acids in the neo acid stream to produce a product stream which includes at least one neo acid ester selectively esterified from the at least one sterically unhindered neo acid, and unreacted neo acids.

27. The method of claim 26, wherein the neo acid stream includes not greater than 50 wt % of the sterically hindered neo acids.

28. The method of claim 26, wherein the sterically unhindered neo acid is pivalic acid.

29. The method of claim 26, wherein the alcohol is methanol.

30. A neo acid ester composition, comprising:
60 to 99 wt % methyl pivalate;
0.25 to 10 wt % $C_6$ to $C_8$ neo acid esters;
0.25 to 20 wt % $C_9$ to $C_{13}$ neo acid esters;
0.25 to 4 wt % $C_6$ to $C_8$ neo acid; and
0.25 to 6 wt % $C_9$ to $C_{13}$ neo acids.

31. The neo acid composition of claim 30, further comprising: 1 to 39 wt % water.

32. The neo acid composition of claim 30, further comprising: 1 to 10 wt % alcohol.

* * * * *